(12) United States Patent
Richard et al.

(10) Patent No.: US 7,914,461 B2
(45) Date of Patent: Mar. 29, 2011

(54) BONE-MARROW EXTRACTION AND/OR INJECTION DEVICE AND A SYSTEM INCLUDING SUCH A DEVICE

(75) Inventors: Patrice Richard, Paris (FR); Christian Schmit, Mareil sur Mauldre (FR)

(73) Assignee: Patrice Richard, Paris (FR)

( * ) Notice: Subject to any disclaimer, the term of this patent is extended or adjusted under 35 U.S.C. 154(b) by 514 days.

(21) Appl. No.: 10/577,428

(22) PCT Filed: Oct. 26, 2004

(86) PCT No.: PCT/FR2004/050536
§ 371 (c)(1),
(2), (4) Date: Aug. 14, 2006

(87) PCT Pub. No.: WO2005/041790
PCT Pub. Date: May 12, 2005

(65) Prior Publication Data
US 2007/0198042 A1   Aug. 23, 2007

(30) Foreign Application Priority Data

Oct. 30, 2003   (FR) .................................... 03 12722

(51) Int. Cl.
*A61B 10/00*   (2006.01)
*A61B 5/00*   (2006.01)
*B65D 81/00*   (2006.01)

(52) U.S. Cl. ........ 600/562; 600/563; 600/565; 600/566; 600/578; 606/80

(58) Field of Classification Search .................. 600/562, 600/563, 564, 565, 566, 567, 576, 578, 579; 606/80
See application file for complete search history.

(56) References Cited

U.S. PATENT DOCUMENTS

| | | | |
|---|---|---|---|
| 4,256,119 A | 3/1981 | Gauthier | |
| 4,445,788 A * | 5/1984 | Twersky et al. | 374/142 |
| 4,641,663 A | 2/1987 | Juhn | |
| 4,922,602 A | 5/1990 | Mehl | |
| 5,322,511 A | 6/1994 | Armbruster et al. | |
| 5,330,443 A | 7/1994 | Powles et al. | |
| 5,478,328 A | 12/1995 | Silverman et al. | |
| 5,571,091 A * | 11/1996 | Davis et al. | 604/164.11 |
| 5,597,536 A | 1/1997 | Mayer | |
| 6,110,176 A * | 8/2000 | Shapira | 606/80 |
| 6,916,292 B2 * | 7/2005 | Morawski et al. | 600/567 |
| 7,179,232 B2 * | 2/2007 | Sutton et al. | 600/567 |
| 2002/0042581 A1 * | 4/2002 | Cervi | 600/567 |
| 2003/0120291 A1 | 6/2003 | Chin et al. | |
| 2003/0176811 A1 | 9/2003 | Shapira | |
| 2004/0249306 A1 * | 12/2004 | Islam | 600/567 |

FOREIGN PATENT DOCUMENTS

FR   2 170 919 A   9/1973

(Continued)

*Primary Examiner* — Max Hindenburg
*Assistant Examiner* — Adam J Eiseman
(74) *Attorney, Agent, or Firm* — Sughrue Mion, PLLC

(57) ABSTRACT

A bone-marrow extraction and/or injection device (1) comprising a grip zone (2), and a needle (10) presenting at least one side orifice (15), a protective sleeve (20) surrounding at least part of said needle (10) being mounted to move relative to said needle (10) between a closed position of said at least one side orifice (15) and an open position of said at least one side orifice.

19 Claims, 3 Drawing Sheets

FOREIGN PATENT DOCUMENTS

| GB | 1 593 101 A | 7/1981 |
| GB | 2 130 890 A | 6/1984 |
| WO | WO 03/101306 A1 | 12/2003 |
| WO | WO 2005/004700 A2 | 1/2005 |

* cited by examiner

BONE-MARROW EXTRACTION AND/OR INJECTION DEVICE AND A SYSTEM INCLUDING SUCH A DEVICE

BACKGROUND OF THE INVENTION

1. Field of the Invention

The present invention relates to a bone-marrow extraction and/or injection device and to an extraction and/or injection system incorporating such a device.

2. Description of the Related Art

Bone marrow is currently extracted by means of a hollow needle (or trocar) presenting an axial orifice through which the bone marrow flows. That type of extraction requires an internal rod (or mandrel) that is inserted into the needle. The function of the rod is to prevent the orifice of the needle from being blocked, in particular by a splinter of bone, during the penetration step in which the needle penetrates into the bone. During the extraction step proper, the rod is removed from the needle and is replaced with a syringe. The user then sucks the bone marrow out by means of the syringe via the orifice of the needle. The sucked-out bone marrow is then transferred into a collection pouch and put into contact with an anticoagulant. Then, the extraction steps are repeated, each time driving the needle provided with the rod further in, in order to collect more bone marrow. That extraction method presents numerous drawbacks. A major drawback is associated with implementing a succession of steps in order to obtain the desired quantity of bone marrow that might be as much as 1.5 liters (L). A typical sequence comprises putting the rod into place, causing the needle to penetrate into the bone, removing the rod, putting the syringe into place, sucking out the bone marrow, removing the syringe, and putting the rod back into place. That sequence needs to be repeated several times. The slow speed and the complexity of the extraction are drawbacks that relate to that type of extraction. That type of extraction mobilizes a large number of people for one to two hours. Generally, one or two doctors perform the extraction, assisted by one or two assistants who are responsible for putting the bone marrow into collection pouches for storage. Another drawback of that type of extraction relates to the successive replacement of the rod with the bone-marrow suction syringe. Thus, the latency time that elapses between removing the rod from the needle and putting the syringe into place means that the bone marrow flowing through the orifice comes into contact with ambient air. Such contact with ambient air can be a source of microbiological contamination of the extracted bone marrow, with the subsequent drawbacks that that implies.

SUMMARY OF THE INVENTION

An object of the present invention is thus to provide a bone-marrow extraction and/or injection device that does not have the above-mentioned drawbacks.

Another object of the present invention is to provide such a device that is also capable of being used in an injection mode, e.g. while transplanting bone marrow from a donor to a recipient.

Another object of the present invention is to provide an extraction and/or injection device that is simple to use, fast, and safe. More particularly, an object of the present invention is to provide an extraction and/or injection device that requires fewer personnel, that reduces the length of time patients are anesthetized, and that ensures that the bone marrow obtained is of good quality, being rich in blood stem cells.

Another object of the invention is to avoid any microbiological contamination of the bone marrow by integrating the extraction and/or injection device of the invention in a sterile extraction and/or injection system.

Another object of the present invention is to provide such a device and system that are simple and inexpensive to manufacture, assemble, and use.

The present invention thus provides a bone-marrow extraction and/or injection device comprising a grip zone, and a needle presenting at least one side orifice, a protective sleeve surrounding at least part of said needle being mounted to move relative to said needle between a closed position of said at least one side orifice and an open position of said at least one side orifice.

Advantageously, said protective sleeve of the device is mounted to turn about the needle.

Advantageously, said protective sleeve of the device includes at least one side opening that is positioned substantially facing said at least one side orifice of the needle in the open position.

Advantageously, said needle of the device is fastened onto a needle holder, said needle holder including reception means that are suitable for co-operating with fastener means of said protective sleeve.

Advantageously, said protective sleeve of the device comprises a first portion constituting a sheath surrounding said needle, and a second portion comprising said fastener means.

Advantageously, said fastener means of the device include at least one claw that is pivotally mounted, and that presents a manual actuation surface and a projection.

Advantageously, said reception means of said needle holder comprise at least one groove that is suitable for receiving at least one projection of said fastener means of said protective sleeve.

Advantageously, said device includes a mixing chamber that is connected to said needle, and to at least one inlet channel and at least one outlet channel.

The present invention also provides a bone-marrow extraction system including such a device.

Advantageously, said system includes a mixing chamber that is connected to said needle of the device, and to at least one inlet channel and at least one outlet channel.

Advantageously, an inlet channel is connected to a source of anticoagulant.

Advantageously, an outlet channel is connected to a bone-marrow collection vessel.

Advantageously, said system includes suction means connected at least to said needle.

Advantageously, said suction means comprise a vacuum pump.

Advantageously, said suction means are controlled by control means, such as a pedal that is actuated by the user.

Advantageously, said inlet channel projects into the mixing chamber and towards said outlet channel, so as to create a Venturi effect.

Advantageously, said system includes a timer device for setting the duration of the bone-marrow suction stages.

The present invention also provides a bone-marrow injection system including such an extraction and/or injection device.

Advantageously, said device is connected to a bone-marrow reservoir, said reservoir being connected to dispenser means.

Advantageously, said dispenser means comprise a pump, such as a syringe with an electrically-driven plunger, or a $CO_2$ pump.

Advantageously, said extraction and/or injection system is packaged in sterile manner.

BRIEF DESCRIPTION OF THE DRAWINGS

Other characteristics and advantages of the invention appear from the following detailed description of a particular embodiment of the invention, given by way of non-limiting example, and with reference to the accompanying drawings, and in which.

DETAILED DESCRIPTION OF THE INVENTION

Figure 1:
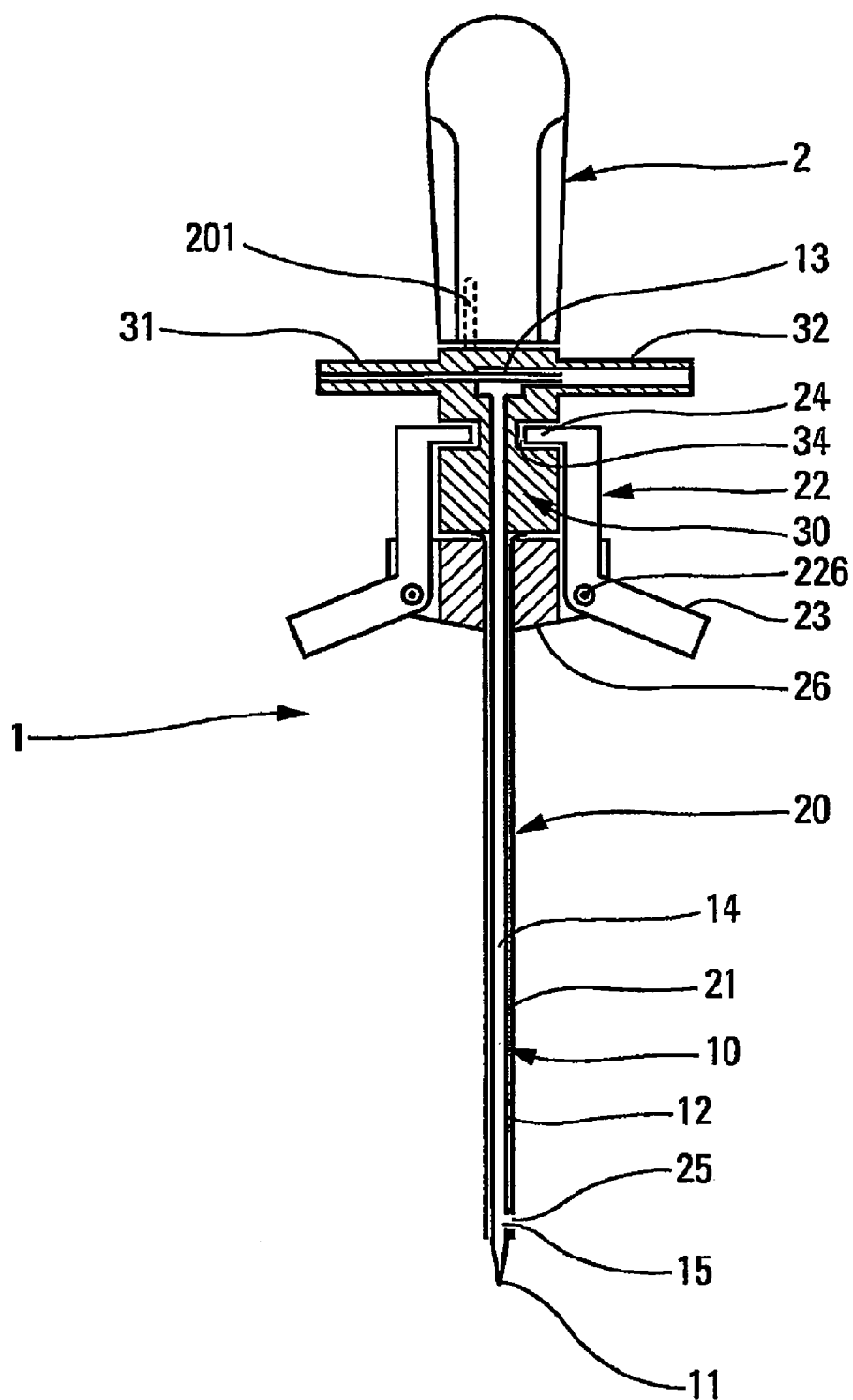
FIG. 1 is a diagrammatic section view of an extraction and/or injection device constituting an advantageous embodiment of the invention.

With reference to FIG. 1, the device 1 of the invention comprises at least a grip zone 2, a needle 10, and a protective sleeve 20. The device as shown can serve both to extract and to inject bone marrow.

The grip zone 2 is a surface that is gripped by the user of the device while bone marrow is being extracted and/or injected. By way of example, the grip zone can be made in the form of a handle, e.g. a handle similar to the handle of a screwdriver. However, the handle can be of any shape and have any characteristics, the present invention not being limited in any way to this particular embodiment, which is given merely by way of example.

Figure 2:
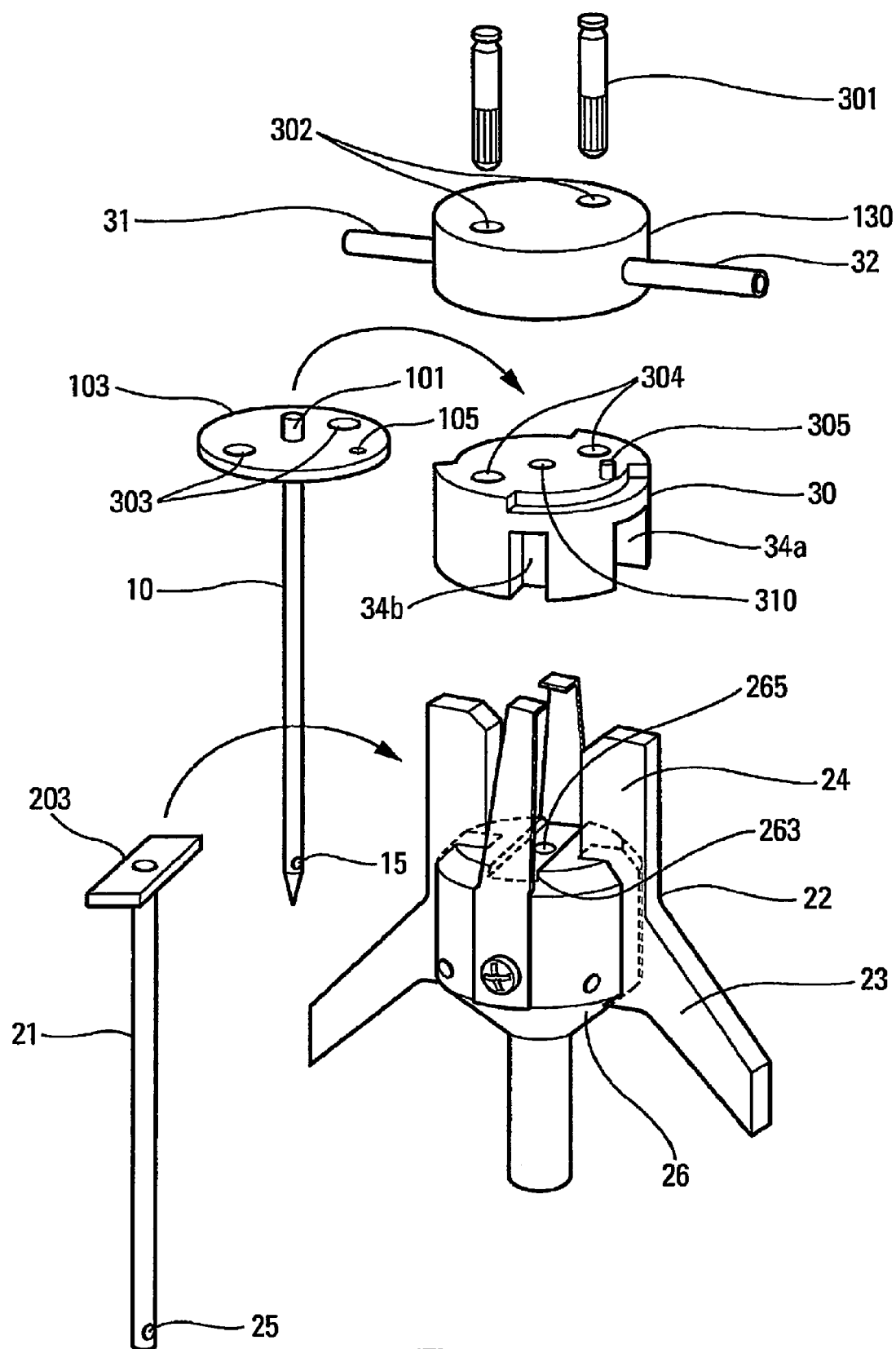
FIG. 2 is a larger-scale exploded perspective view of a portion of the FIG. 1 extraction and/or injection device.

The needle 10 is in the form of a cylindrical hollow body 12 that is terminated by a point 11 that is adapted to pierce bone. The needle presents a flow duct 14. In the invention, the needle includes at least one, and advantageously two, side orifices 15, formed near to the point 11, and advantageously at the end of the cylindrical body 12. It should be noted that the orifices formed in the body of the needle can be of any shape. The needle 10 advantageously co-operates with a needle holder 30. The needle holder can be made integrally with the needle, or, as shown in FIG. 2, it can be made separately, being separable, and co-operating by mutual engagement as described more fully below.

The protective sleeve 20 advantageously comprises firstly a first portion forming a sheath 21, and secondly a second portion comprising fastener means 22. The sheath 21 constitutes an advantageously cylindrical casing surrounding all or part of the needle 10. The needle can thus be surrounded over a fraction only of its length, or over a fraction only of its width, providing said sheath co-operates with said at least one side orifice 15 of the needle. In the invention, the sleeve 20 is mounted to move relative to the needle 10 between a closed position of said at least one side orifice and an open position of said at least one side orifice 15. The sheath 21 advantageously includes at least one side opening 25 that can be moved into co-incidence with a respective side orifice 15 of the needle in the open position. The side opening 25 preferably presents a shape that corresponds to the shape of the side orifice 15 of the needle, but a different shape can also be envisaged. Various combinations of shapes can thus be envisaged, making it possible to bring the side orifice(s) 15 of the needle into register with the side opening(s) 25 of the sheath, thereby defining one or more through holes via which the bone marrow can pass while it is being extracted or injected.

The fastener means 22 of the protective sleeve 20 advantageously present an overall shape in the form of fins or claws. In a preferred embodiment of the invention, the device includes two fastener means 22 that are situated substantially facing each other. The fastener means 22 can comprise firstly a manual actuation surface 23, and secondly a projection 24. The fastener means 22 are advantageously mounted on a fastener bushing 26. The fastener bushing 26 and the sheath 21 of the protective sleeve 20 could be made as a single part. However, in the embodiment in FIG. 2, the two elements are made separately, being separable, and they co-operate by mutual engagement as described more fully below. Each fastener means 22 can form a lever that is capable of pivoting about a respective axis 226 between a fastened position and a released position. The manual actuation surface 23 of said fastener means advantageously projects outwards so as to make it easier for the user to manipulate the protective sleeve 20. The projections 24 serve as fastener surfaces for fastening said protective sleeve 20 to the device of the invention. In the embodiment shown, the projections 24 of the fastener means 22 co-operate with reception means 34. The reception means 34 are advantageously in the form of grooves that are formed radially in the needle holder 30. The needle holder 30 can co-operate with the grip zone (or handle) 2 to form a single unit. The grooves 34 can be four in number and can be distributed in two pairs 34a, 34b. Each pair 34a, 34b comprises two grooves that are opposite each other so as to enable them to co-operate with two claws 22 that are also opposite each other. Since the protective sleeve is mounted to move relative to the needle 10, the projections 24 are thus positioned in one pair of grooves 34 or the other depending on the selected position (closed or open). The protective sleeve 20 is preferably displaced by turning the protective sleeve 20 about the needle 10. To do this, the user releases the projections 24 of the claws 22 from the first pair of grooves 34a, turns the protective sleeve 20 about the needle 10, and then positions the projections 24 of the claws 22 in the other pair of grooves 34b. Thus, in the "open" first position, each side orifice 15 of the needle is disposed facing a respective side opening 25 of the protective sleeve. This position thus results in the creation of a through hole via which bone marrow can be extracted and/or injected. In the "closed" second position, no side orifice 15 of the needle is open, and, on the contrary, any side orifice is covered by the sheath 21 of the sleeve 20. Thus, in this event, no through hole is defined via which bone marrow can be extracted and/or injected, therefore preventing any extraction or injection. This second position therefore corresponds to the position used when causing the needle 10 to penetrate into the bone. In this way, there is no risk of the orifice(s) 15 of the needle 10 becoming blocked while said needle is being inserted into the bone.

It should be noted that the above-described embodiment constitutes an advantageous embodiment of the invention, and that various variants can be envisaged. For example, the displacement of the protective sleeve 20 from the closed position to the open position (and vice-versa) could be done by displacing the protective sleeve axially, or by combining both a turning movement with an axial displacement movement. In addition, the fastener means 22 of the sleeve 20 could be made in some other way, and could, for example, incorporate indicator means for clearly indicating to the user the position of the sleeve relative to the needle.

In a preferred embodiment of the invention, the device includes a mixing chamber 13. The mixing chamber 13 is connected to the duct 14 of the needle, to at least one inlet channel 31, and to at least one outlet channel 32. The duct 14 of the needle conveys the extracted bone marrow. Said at least one inlet channel 31 can convey an anticoagulant, such as heparin, that serves to avoid blood clots forming in the extracted bone marrow. Said at least one outlet channel 32 thus contains a mixture of anticoagulant and bone marrow, and can lead to a collection vessel. The inlet and outlet channels 31 and 32 are advantageously disposed on either side of the mixing chamber 13. In a variant, it is possible to envisage that the mixing chamber and said at least one inlet channel and at least one outlet channel are made separately from the extraction and/or injection device.

Said at least one inlet channel 31 advantageously projects into the mixing chamber 13, and can even be positioned directly at least one outlet channel 32. This type of disposition favors creating a Venturi effect, consequently improving mixing of the bone marrow with the anticoagulant mixture at said at least one outlet channel 32. This improved mixing therefore assists in obtaining better quality bone marrow.

FIG. 2 shows an embodiment of the invention in which the mixing chamber 13 is formed in a add-on element 130 that co-operates with the needle holder 30. In this embodiment, fastener pegs 301 are inserted into holes 302, 303, 304 that are respectively formed in said add-on element 130, the needle 10, and the needle holder 30 so as to obtain a single unit. It is also possible to envisage that the pegs 301 co-operate with holes 201 provided in the handle 2, in order to fasten it to the unit. In this embodiment, the needle 10 can be provided with a platform 103 enabling the needle to be held on the needle holder 30. The platform is positioned in such a manner as to leave a portion 101 of the needle 10 free to reach the mixing chamber 13. This free portion therefore puts the duct 14 of the needle into contact with the mixing chamber 13.

In order to make it easier to put the needle 10 into place on the needle holder 30, indexing means can be provided. By way of example, the indexing means can be made up of a hole 105 formed in the platform 103 of the needle, and co-operating with a projection 305 on the needle holder. Thus, while the needle 10 is being inserted into the central orifice 310 of the needle holder, the platform is thus positioned in such a manner that the projection 305 becomes engaged in the hole 105. As a result of this positioning, the holes 303 and 304 are in alignment, thereby making it easier to insert the fastener pegs 301. In addition, indexing means for putting the add-on element 130 into place on the platform 103 can be provided in order to bring the holes 302 into alignment with the holes 303 and 304.

As described above, the sheath 21 of the protective sleeve can be a part that is added on. In this event, the sheath 21 is inserted into an orifice 265 passing through the fastener bushing 26. The protective sleeve 20 is held by means of a crossbar 203 that is positioned in a housing 263 of complementary shape, formed in the fastener bushing.

The embodiment described above with reference to FIGS. 1 and 2 is advantageous in that the device is easy to assemble and to disassemble. The device can therefore be packaged in unassembled and sterile manner in a single package. During use, the user inserts the sheath 21 of the sleeve 20 into the orifice 265 of the bushing 26. The user then places the needle 10 in the needle holder 30, and the unit is assembled on the bushing 26, the needle 10 passing into the sheath 21.

The mixing chamber 13 provided in the add-on element 130 can optionally be assembled on the needle holder 30 by means of the pegs 301, before assembling the needle holder 30 on the bushing 26. In addition, the handle 2 can be pre-assembled using said pegs 301.

Naturally, this embodiment is only an example. In particular, various elements described above could be made as a single part, so as to limit the number of parts to be assembled. For example, the mixing chamber 13 could be formed in the needle holder 30, and the needle 10 could be made integrally with said needle holder 30. The mixing chamber 13 could also be formed in the handle 2. The sleeve 20 could also be made as a single part. The essential idea is to make a sleeve 20 that can be displaced relative to the needle 10 between its closed and open positions.

The present invention also relates to an extraction and/or injection system that integrates an extraction and/or injection device 1 as described above.

Figure 3:
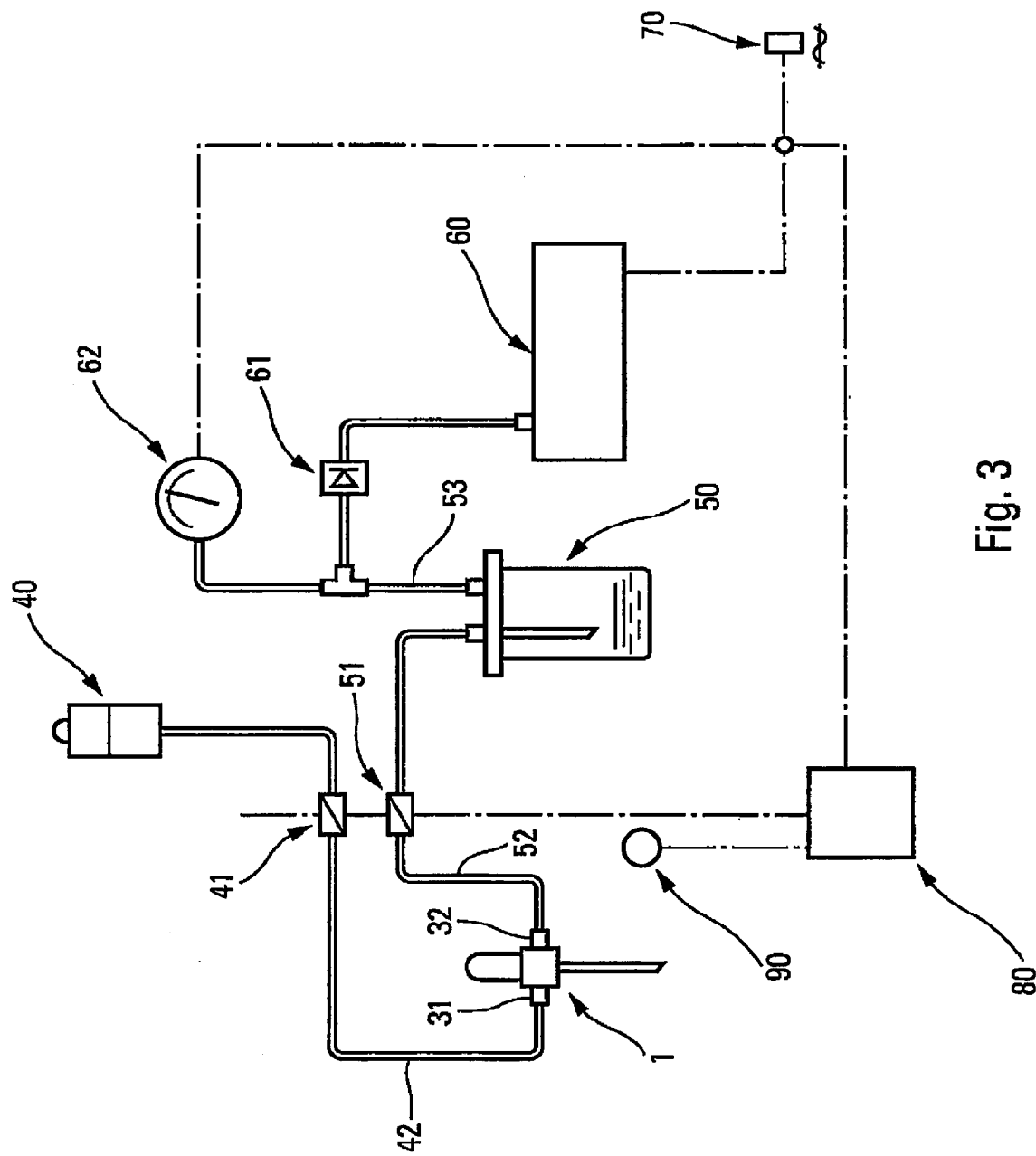
FIG. 3 is a diagrammatic view of an extraction and/or injection system constituting an embodiment of the invention.

FIG. 3 presents a preferred embodiment of the extraction system. In this embodiment, an inlet channel 31 of the device is connected to an anticoagulant source 40 via a tube 42. An outlet channel 32 is itself connected to a bone-marrow collection vessel 50 via a tube 52. Respective solenoid valves 41 and 51 can be placed on tubes 42 and 52, respectively for controlling the anticoagulant content, and the quantity of extracted bone marrow mixed with anticoagulant. The collection vessel 50 is preferably in communication with suction means 60. The suction means can be formed by a vacuum pump that is connected to an electrical connection 70. The vacuum pump creates suction, causing the anticoagulant and the extracted bone marrow to be sucked into the collection vessel 50. In a variant, it is possible to use a peristaltic pump, or any other appropriate suction means. The system is advantageously controlled by a single control means, controlling both the opening and the closing of the solenoid valves 41 and 51. The control means 90 can be a pedal that is actuated by the user. An anti-return device 61 can be placed in a tube 53 that connects the collection vessel 50 to the suction means 60. The purpose of the anti-return device 61 is to prevent any of the anticoagulant and bone marrow mixture from being sucked from the collector 50 to the suction means 60. A pressure gauge 62 can also be integrated in the extraction system. The gauge 62 can thus intervene to close the solenoid valves 41 and 51 on reaching a predetermined vacuum threshold that is preferably less than 900 millibars (mb). The gauge 62 thus makes it possible to obtain effective and strong suction as soon as the valves are opened, favoring better separation of the hematopoietic progenitors, and thus obtaining richer bone marrow. Furthermore, the system can integrate a timer device 80 for the purpose of setting, and in particular limiting, the duration of the bone marrow extraction. Other control means for determining certain characteristics of the extraction could be envisaged. Amongst these characteristics, duration, intensity, flowrate, frequency, etc. should also be noted.

The present invention also relates to an injection system that can be used for transplanting bone marrow into the trabeculae of spongy bone. In this event, the device 1 is merely connected to a bone-marrow reservoir of the syringe type. The syringe can be actuated manually, or it can be connected to pump-type dispenser means, e.g. a syringe with an electrically-driven plunger, or any other type of pump, such as a $CO_2$ pump, or to any other optionally-electric control system. Such means thus ensure complete control of the speed and of the quantity of bone marrow to be transplanted.

When the device is used in an injection system, the inlet channel 31 of the mixing chamber 13 is preferably closed. For example, the channel 31 can be removed and the resulting hole blocked by any suitable means. The mixing chamber 13 thus advantageously becomes a mere transit chamber for the bone marrow.

The extraction and/or injection device and the extraction and/or injection system of the invention are advantageously supplied in the form of a kit. The parts that make up the kit are advantageously packaged in sterile manner, thereby avoiding any microbiological contamination.

Although the invention is described above with reference to a particular embodiment thereof, naturally it is not limited by said embodiment, but on the contrary, any useful modifications can be applied thereto by the user, without going beyond the ambit of the present invention, as defined by the accompanying claims.

The invention claimed is:

1. A bone-marrow extraction system, comprising:
   a bone-marrow extraction and/or injection device comprising:
      a grip zone; and
      a needle presenting at least one side orifice;
      wherein said needle is fastened onto a needle holder, and a protective sleeve surrounds at least part of said needle, said protective sleeve being mounted to move relative to said needle between a closed position of said at least one side orifice and an open position of said at least one side orifice, and said needle holder including reception means that are suitable for co-operating with fastener means of said protective sleeve so as to hold said protective sleeve in the closed position or in the open position; and
      said fastener means include a pair of claws disposed diametrically opposite to one another, each claw being pivotally mounted, and presenting a manual actuation surface and a projection; and
   a mixing chamber that is connected to said needle of the device, and to at least one inlet channel and at least one outlet channel;
   wherein an inlet channel is connected to a source of anticoagulant.

2. An extraction system according to claim 1, in which said protective sleeve is mounted to turn about the needle.

3. An extraction system according to claim 1, in which said protective sleeve includes at least one side opening that is positioned substantially facing said at least one side orifice of the needle in the open position.

4. An extraction system according to claim 1, in which said protective sleeve comprises a first portion constituting a sheath surrounding said needle, and a second portion comprising said fastener means.

5. An extraction system according to claim 4, in which said reception means of said needle holder comprise at least one groove that is suitable for receiving at least one projection of said fastener means of said protective sleeve.

6. An extraction system according to claim 1, in which said device includes a mixing chamber that is connected to said needle, and to at least one inlet channel and at least one outlet channel.

7. An extraction system according to claim 6, in which said mixing chamber is provided in the needle holder.

8. An extraction system according to claim 6, in which said grip zone comprises a handle, said mixing chamber being provided in said handle.

9. An extraction system according to claim 6, including an add-on element between said grip zone and said needle holder, said mixing chamber being provided in said add-on element.

10. An extraction system according to claim 1, in which an outlet channel is connected to a bone-marrow collection vessel.

11. An extraction system according to claim 1, in which said system includes suction means connected at least to said needle.

12. An extraction system according to claim 11, in which said suction means comprise a vacuum pump.

13. An extraction system according to claim 11, in which said suction means are controlled by a control means comprising a pedal that is actuated by the user.

14. An extraction system according to claim 1, in which said at least one inlet channel projects into the mixing chamber and towards said at least one outlet channel, so as to create a Venturi effect.

15. An extraction system according to claim 1, in which said system includes a timer device for setting the duration of the bone-marrow suction stages.

16. An extraction system according to claim 1, wherein said device is also configured for bone-marrow injection, and is connected to a bone-marrow reservoir, said reservoir being connected to dispenser means.

17. An extraction system according to claim 16, in which said dispenser means comprise a pump comprising a syringe with an electrically-driven plunger, or a $CO_2$ pump.

18. An extraction and/or injection system according to claim 1, in which said system is packaged in sterile manner.

19. A bone marrow extraction and/or injection device according to claim 1, wherein the fastener means prevents a radial force from being applied to the protective sheath.

* * * * *